Figure 1:
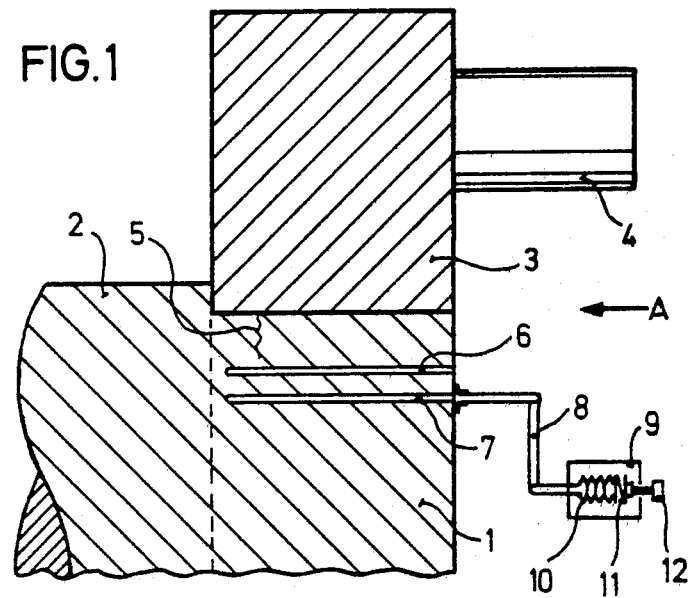

United States Patent [19]

Dressel et al.

[11] 4,448,080

[45] May 15, 1984

[54] PROCESS AND APPARATUS FOR MONITORING THE FORMATION AND PROPAGATION OF CRACKS IN MACHINE PARTS AND COMPONENTS

[75] Inventors: Manfred Dressel, Lambsheim; Johannes Greven, Lampertheim; Arnulf Jeck, Neustadt; Rudolf Magin, Schifferstadt; Günther Nick, Neuhofen; Paul Schaffarczyk, Speyer; Guenther Weiss, Wachenheim, all of Fed. Rep. of Germany

[73] Assignee: BASF Aktiengesellschaft, Ludwigshafen, Fed. Rep. of Germany

[21] Appl. No.: 330,026

[22] Filed: Dec. 11, 1981

[30] Foreign Application Priority Data

Dec. 31, 1980 [DE] Fed. Rep. of Germany ....... 3049628

[51] Int. Cl.³ .............................................. G01N 19/08
[52] U.S. Cl. ........................................... 73/799; 73/40
[58] Field of Search ..................... 73/40, 49.7, 104, 37, 73/40.7, 799

[56] References Cited

U.S. PATENT DOCUMENTS

| | | | |
|---|---|---|---|
| 2,185,315 | 1/1940 | Rogatchoff | 73/40 UX |
| 3,557,620 | 1/1971 | Jewett et al. | 73/756 |
| 4,092,696 | 5/1978 | Boesen et al. | 73/753 X |
| 4,254,415 | 3/1981 | Kaufman | 73/37 X |

*Primary Examiner*—Jerry W. Myracle
*Attorney, Agent, or Firm*—Keil & Witherspoon

[57] ABSTRACT

For the purpose of monitoring the formation and propagation of cracks in machine parts and components, especially in the rotating shafts of prime movers and mechanical equipment, at least one hole is drilled in the uncracked section of the component, this drilled hole intersecting the plane of the crack which is to be expected and being filled with a gas or a liquid, the gas or liquid being adjusted to a pressure above the ambient pressure, and the drilled hole being provided with a closure with respect to the environment and being connected, via a line, to an instrument for indicating a fall in the pressure of the medium present in the drilled hole.

6 Claims, 5 Drawing Figures

PROCESS AND APPARATUS FOR MONITORING THE FORMATION AND PROPAGATION OF CRACKS IN MACHINE PARTS AND COMPONENTS

The present invention relates to a process and apparatus for monitoring the formation and propagation of cracks in machine parts and components, especially in the rotating shafts of prime movers and mechanical equipment. This type of monitoring is important, since fractures of such machine parts and components commonly give rise to incidents involving major damage, which entails complicated repairs, expensive replacements and, in some cases, long shut-down times.

The testing of machine parts and components for cracks is the subject of the procedures known as non-destructive materials testing. Numerous such procedures have been developed, the most important examples being radiography, using X-rays and gamma radiation, the ultrasonic inspection method, the dye penetration and diffusion method, the electric induction and magnetic induction method, the use of resistance strain gauges and break-wires, the acoustic testing technique and the vibration measurement technique. Many of these techniques share the characteristic that it is impossible to carry out the test procedure while the component is rotating, so that testing can only be carried out intermittently and it is necessary to shut down the unit before each test and, under some circumstances, to remove the component in question. In the case of the acoustic test, the presence of cracks manifests itself by a change in the sound when the component is struck. However, it is often impossible to strike components while they are in operation, or their size may be such that a crack gives rise to no detectable acoustic change. In the case of vibration measurements on components, changes in amplitude or frequency are detected, from which conclusions are drawn with regard to changes in the component. Although vibrations can be measured comparatively accurately, the technique fails if, for example, a crack forms beneath a second component which is shrunk onto the first component, since, in this case, no detectable change in vibration occurs, because of the supporting effect of the second component. Moreover, there is the disadvantage that, in the case of parts which are rotating, the vibration of a component, eg. of a bearing block, can be measured only indirectly.

All known procedures possess the disadvantage that they can be employed only to a limited extent, especially in the case of machine parts which are rotating, of hidden cracks or of specific materials, or in areas which are subject to explosion hazards, and that continuous monitoring, with transmission of the measurement signal, is impossible.

It is an object of the present invention to provide a process and apparatus which enable the formation of a crack in a fixed or moving component to be determined, enable the propagation of a crack to be continuously monitored, and generate an indication of both the formation and the propagation of the crack by employing a measuring device.

We have found that this object is achieved, according to the invention, by means of a procedure in which at least one zone, through which a medium can permeate, is provided in the uncracked section of the component, this zone intersecting the plane of the crack which is to be expected and being filled with a medium, the medium being adjusted to a defined pressure which deviates from the ambient pressure, and the permeable zone being closed off with respect to the environment and being conductively connected to a device for indicating a change in pressure caused by the crack.

In an advantageous further development of the invention, the permeable zone is produced in the form of a drilled hole, the medium which is introduced into the drilled hole being adjusted, by compression or evacuation, to a pressure above or below the ambient pressure, and the drilled hole being provided with a closure with respect to the environment and being connected, via a line, to an instrument for indicating a change, caused by the crack, in the pressure of the medium present in the drilled hole.

In order to increase the fall or rise in pressure, it is possible to drill at least one venting hole in the uncracked section of the component, or in the section which has already cracked, this venting hole intersecting the plane of the crack which is to be expected and being located between the existing or expected incipient crack and the drilled hole.

The instrument for indicating a fall or rise in pressure can be designed in the form of a pressure/displacement converter, which is equipped either with a contactless measuring system for indicating a change in pressure, or with a contact-type transmitter for indicating that the change in pressure has exceeded a limiting value.

As an additional measure for indicating a fall in pressure, and hence for indicating that a crack has undergone a change, it is possible to provide a buffer vessel between the drilled hole and the instrument for indicating a fall in pressure, this buffer vessel being subject to the same pressure as the drilled hole.

Gases and liquids can be used as the medium.

The details of the invention are represented in the drawing, by reference to two illustrative embodiments, and are described more comprehensively in the text which follows.

Figure 2:
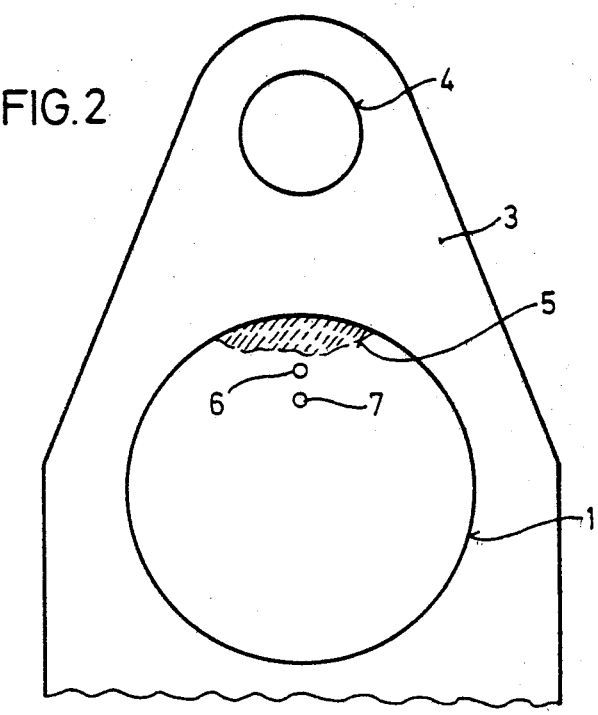
Figure 3:
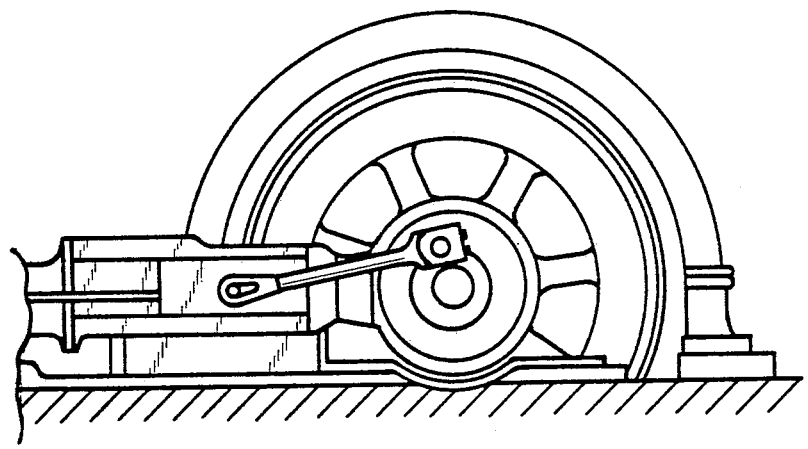
Figure 5:
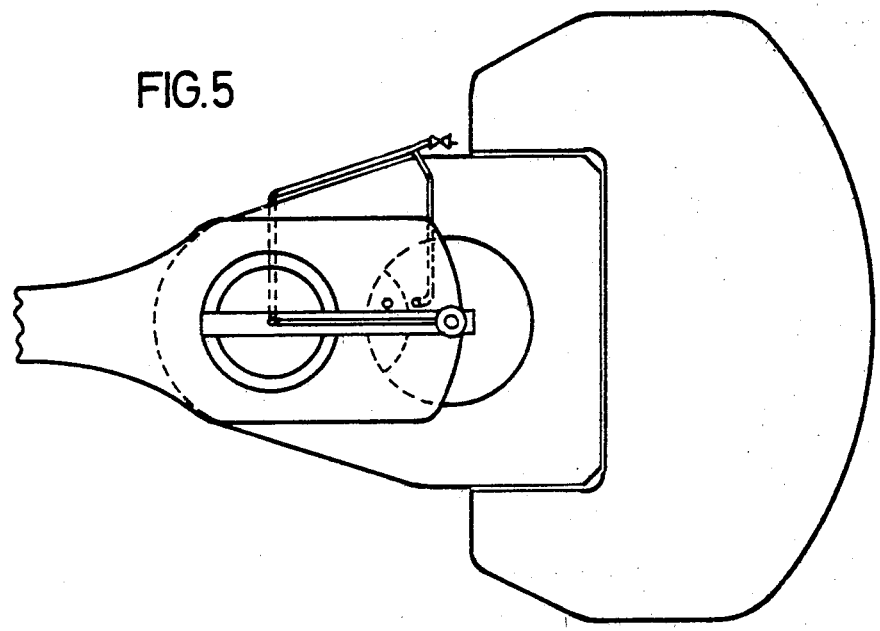
Figure 4:
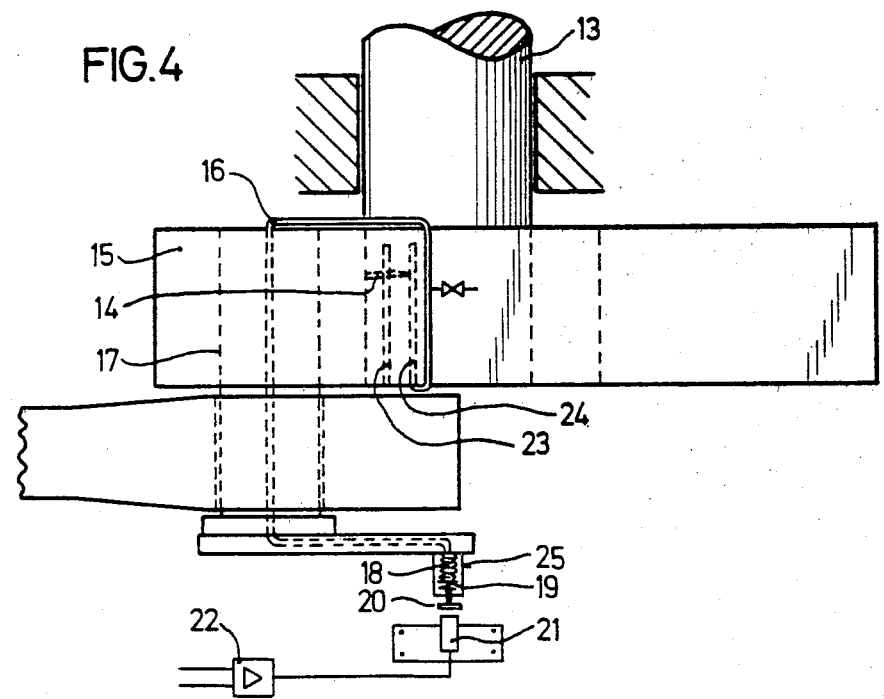

In the drawing:

FIG. 1 shows a longitudinal section of a crankshaft with a shrunk-on crank web and a device for detecting a change in pressure FIG. 2 shows a projected view of a crank web which has been shrunk onto a crankshaft FIG. 3 shows a side view of a piston-type compressor FIG. 4 shows a partial section of the piston-type compressor represented in FIG. 3, and a device for detecting a change in pressure FIG. 5 shows a partial view of the piston-type compressor illustrated in FIG. 3.

In accordance with FIGS. 1 and 2, the crank web 3 is shrunk onto the crank journal 1 of a crankshaft 2. The crank pin 4 is shrunk into the crank web 3. A crack 5 lies beneath the crank web 3, and is hidden by this crank web. A venting hole 6 and a hole 7, the latter being connected to a system 8 of tubes, are drilled beneath the line of the fracture. The drilled hole 7 is connected to a pressure/displacement converter 9, via the system 8 of tubes. This pressure/displacement converter 9 is assembled from a pressure-measuring bellows 10, a counter-spring 11, and a transmitting device 12 for contactless pick-off.

The drilled hole 7, the system 8 of tubes, and the pressure-measuring bellows 10 are pressurized and closed in a leakproof manner. The drilled venting hole 6 remains unpressurized. When the crack-front 5 propagates as far as the drilled hole 7, a fall in pressure occurs in the drilled hole 7, in the system 8 of tubes, and in the pressure-measuring bellows 10. This fall in pressure is converted, with the aid of the pressure/displacement converter 9, into a change in displacement, and the transmitting device 12 is moved towards the pressure-measuring bellows 10. This change in displacement is measured, in a contactless manner, inductively, capacitatively, pneumatically or hydraulically, using conventional, commercially available measuring and control instruments. At the same time, the drilled hole 6 contributes to a more rapid rate of change of pressure.

In another illustrative embodiment, represented in FIGS. 3 to 5, it was necessary, in the case of a piston-type nitrogen compressor having a crankshaft 13 which had already started to crack, to monitor the propagation of the crack 14, since major damage could occur if operation of the compressor were to be continued without supervision and the crankshaft were to fracture suddenly. The incipient crack, located beneath the shrunk-on crank web 15, had previously been found by means of the ultrasonic measuring technique, while the machine was shut down. In this case, the assembly of the pressure system 16, manufactured from 3 mm diameter high-pressure tubing, was rendered difficult by the fact that the tubing had to be routed behind the crank web 15 and led through the crank pin 17, in order to enable the measured value to be transmitted coaxially with the motor shaft. In the case of motors and turbocompressors, it is possible to dispense with this complicated assembly of the pressure system 16. The pressure system 16 is connected to a pressure/displacement converter 25, the latter being assembled from a pressure-measuring bellows 18, a counter-spring 19, and a transmitting device 20 for contactless pick-off. A commercially available electric/inductive pick-up is used as the contactless transducer 21, this device being coupled, in turn, to a conventional measurement amplifier 22 for annunciating and switching purposes.

When the crack 14 propagates further beyond the drilled venting hole 23, as far as the drilled hole 24, which is connected to the pressure system 16, the confined, compressed medium expands, via the crack 14 which has propagated and the drilled venting hole 23. This causes the pressure-measuring bellows 18 in the pressure/displacement converter 25 to be compressed by the counterspring 19, and the transmitting device 20 for contactless pick-off to be moved towards the crankshaft. This movement is electrically/inductively measured in the transducer 21, and the change in the current flow is utilized, by means of a conventional measurement amplifier 22, for annunciating the danger and switching off the compressor.

The advantages which can be achieved by means of the invention can be seen to reside especially in the fact that hidden cracks, which cannot be seen from the outside, can be continuously monitored during operation, even in components which are rotating, by means of conventional measures, without maintenance, and irrespective of the material. Only a very small space is necessary for this purpose. The medium which triggers the measurement signal needs to be introduced only once, and no energy losses need to be made good.

Possible applications of the invention arise in the case of any components which are subject to the risk of cracking or fracture, eg., motor shafts, crankshafts, rolling-mill shafts, crane tracks, girders and supports.

We claim:

1. A method for continuously monitoring the formation and propagation of cracks in movable machine parts and components during the operation thereof, especially in the rotating shafts or prime movers and mechanical equipment, said method comprising
   providing in the uncracked section of the component at least one zone which is permeable to a medium and which intersects the plane of the crack,
   filling said zone with a medium and adjusting said medium to a defined pressure which deviates from the ambient pressure,
   closing off said zone with respect to the environment,
   providing outside of said component a pressure responsive means,
   connecting said pressure responsive means by a line to said zone for communication therewith, and
   deriving from the displacement of said pressure responsive means an indication of a change in pressure caused by the crack.

2. An apparatus for continuously monitoring the formation and propagation of cracks in movable machine parts and components during the operation thereof, especially in the rotating shafts of prime movers and mechanical equipment,
   wherein at least one bore is provided in the uncracked section of the component, said bore intersecting the plane of the crack which is to be expected, being filled with a medium, gaseous or liquid, which is adjusted to a pressure above or below the ambient pressure and being closed off with respect to the environment,
   wherein a pressure responsive means is provided outside of said component, and a line interconnecting said bore with said pressure responsive means, the displacement of said pressure responsive means being indicative of a fall or rise in the pressure of the medium present in said bore, and
   wherein, in order to augment the fall or rise in pressure, at least one venting hole is provided in the uncracked section of the component or in the section which has already cracked, said venting hole intersecting the plane of the crack which is to be expected, and being located between the existing or expected incipient crack and said bore.

3. An apparatus as claimed in claim 2, wherein said medium is a gas adjusted to a pressure below the ambient pressure, the displacement of said pressure responsive means being indicative of a rise in the pressure of the gas present in said bore.

4. An apparatus as claimed in claim 2, wherein said pressure responsive means is equipped with a contactless measuring system for indicating the change in pressure.

5. An apparatus as claimed in claim 2, wherein said pressure responsive means is equipped with a contact-type transmitter for indicating that the change in pressure has exceeded a limiting value.

6. An apparatus as claimed in claim 2, wherein a buffer vessel is provided between said bore and said pressure responsive means, said buffer vessel being subject to the same pressure as said bore.

* * * * *